United States Patent
Rudloff et al.

(10) Patent No.: US 7,227,029 B2
(45) Date of Patent: Jun. 5, 2007

(54) METHOD FOR THE CONTINUOUS PRODUCTION OF N-METHYL-2-PYRROLIDONE (NMP)

(75) Inventors: Martin Rudloff, Weisenheim (DE); Peter Stops, Altrip (DE); Erhard Henkes, Einhausen (DE); Helmut Schmidtke, Bensheim (DE); Rolf-Hartmuth Fischer, Heidelberg (DE); Manfred Julius, Limburgerhof (DE); Rolf Lebkücher, Mannheim (DE); Karl-Heinz Ross, Grünstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 513 days.

(21) Appl. No.: 10/495,358

(22) PCT Filed: Nov. 15, 2002

(86) PCT No.: PCT/EP02/12804

§ 371 (c)(1),
(2), (4) Date: May 11, 2004

(87) PCT Pub. No.: WO03/053924

PCT Pub. Date: Jul. 3, 2003

(65) Prior Publication Data

US 2005/0010057 A1    Jan. 13, 2005

(30) Foreign Application Priority Data

Nov. 20, 2001 (DE) ................. 101 56 885

(51) Int. Cl.
 *C07D 207/12* (2006.01)
 *C07D 307/20* (2006.01)

(52) U.S. Cl. ...................... 548/543; 549/313

(58) Field of Classification Search ................ 548/543; 549/313

See application file for complete search history.

(56) References Cited

U.S. PATENT DOCUMENTS

| 2,964,535 A | 12/1960 | Clements |
| 3,775,431 A | 11/1973 | Rodewald |
| 3,975,499 A | 8/1976 | Himmele et al. |

FOREIGN PATENT DOCUMENTS

| DE | 1 795 007 | 7/1968 |
| EP | 1 004 577 | 5/2000 |
| WO | 99/52867 | 10/1999 |

OTHER PUBLICATIONS

Ullmann's Encyclopedia of Industrial Chemistry, 5th Ed., vol. A22, pp. 458-459 1993.
Winnacker, Kuechler, "Chemische Technologie," 4th Ed., vol. 6, p. 99.
Chem. Abstracts 77:61805 and Derwent Abstr. 40726T-E 1997.
Chem. Abstracts 124:145893 = CN-A-110 46 35 1997.
Chem. Abstracts 129:67694 = JP-A2-10 158 238 1998.
Derwent Abstract 97-234193/21 = RO-B1-111 189 1997.
Derwent Abstract 1998-607722 and Chem. Abstracts 134:178463 = RO-B1-113 640.
Chem. Abstract 82:139947 = JP-B4-49 020 585 1982.
Chem. Abstract 87:5802 = JP-A2-49 041 364 1987.

*Primary Examiner*—Kamal A. Saeed
*Assistant Examiner*—Michael Barker
(74) *Attorney, Agent, or Firm*—Novak Druce & Quigg, LLP

(57) ABSTRACT

Process for the continuous preparation of N-methyl-2-pyrrolidone (NMP) by reacting gamma-butyrolactone (GBL) with monomethylamine (MMA) in the liquid phase, wherein GBL and MMA are used in a molar ratio of from 1:1.08 to 1:2 and the reaction is carried out at from 320 to 380° C. and an absolute pressure of from 70 to 120 bar.

17 Claims, No Drawings

METHOD FOR THE CONTINUOUS PRODUCTION OF N-METHYL-2-PYRROLIDONE (NMP)

The present invention relates to a process for the continuous preparation of N-methyl-2-pyrrolidone (NMP) by reacting gamma-butyrolactone with monomethylamine in the liquid phase.

Owing to particular advantageous properties, NMP is an important, versatile solvent and reaction medium for the chemical industry (Ullmann's Encyclopedia of Industrial Chemistry, 5$^{th}$ Ed., Vol. A22, pages 458 to 459).

As indicated in Ullmann's Encyclopedia of Industrial Chemistry, 5$^{th}$ Ed., (see above), NMP is prepared mainly by reacting gamma-butyrolactone (GBL) with methylamine in a shaft reactor (high-pressure tube with special guide plates) at from 200 to 350° C. and about 10 MPa (=about 100 bar).

Winnacker, Küchler, "Chemische Technologie", 4th edition, 1982, Volume 6, state on page 99, lines 5–9, that gamma-butyrolactam (2-pyrrolidone) is prepared from GBL by complete reaction with liquid ammonia at 270° C. and about 120 bar, e.g. in a cascade of three stirred reactors (selectivity: 94 mol %) (DE-A-17 95 007) and that NMP is formed in an analogous reaction with methylamine.

Chem. Abstracts 77:61805 and Derwent Abstr. 40726T-E (JP-B4-47 021 420) relate to the preparation of NMP by reacting GBL with MeNH$_2$ in the presence of water. The batchwise reaction of GBL with MeNH$_2$ and water in a molar ratio of 1:2:2–4 at 250° C. (2–1.5 h) gives NMP in a yield of 99%. Without the presence of water in the synthesis, the yield is only 96% (1.5 h).

Chem. Abstracts 124:145893 (CN-A-110 46 35) describes the synthesis of NMP by reaction of GBL with MeNH$_2$ at 220–290° C. and ≧6 MPa (≧60 bar). The batchwise reaction of a mixture of GBL, 30% strength aqueous MeNH$_2$ and water in a weight ratio of 1:1.4:5.6 at 280° C. and 6 MPa (60 bar) gives NMP in a yield of 97%. The above weight ratio corresponds to a molar ratio of GBL:MeNH$_2$:H$_2$O of 1:1.2:26.7 (without taking the water in the MeNH$_2$ solution into account) or a molar ratio of 1:1.2:31.5 (when the water in the MeNH$_2$ solution is taken into account).

Chem. Abstracts 129:67694 (JP-A2-10 158 238) relates to the reaction of GBL with from 1.03 to 1.50 molar equivalents of MeNH$_2$ in the presence of from 1.0 to 2.9 molar equivalents of water at from 250 to 300° C. The batchwise reaction of GBL with MeNH$_2$ and water in a molar ratio of 1:1.1:1 at 280° C. (1 h) gives NMP in a yield of 99.9%.

Derwent Abstract 97-234193/21 (RO-B1-111 189) describes a two-stage continuous process for preparing NMP from GBL and MeNH$_2$ in the presence of water.

The reaction conditions in the first stage are: molar ratio of GBL, MeNH$_2$ and water=1:1.2:2.1, (0.5 to 2)×10$^4$ N/m$^2$ (=0.05 to 0.2 bar (gauge pressure)) and from 40 to 50° C.

The reaction conditions in the second stage are: 280 to 290° C. and (90 to 100)×104 N/m$^2$ (=9 to 10 bar (gauge pressure)).

Derwent Abstract 1998-607722, Chem. Abstracts 134:178463 (RO-B1-113 640) relate to a process for the continuous preparation of NMP in the liquid phase in a two-stage procedure. The reaction conditions in the first stage are: molar ratio of GBL, MeNH$_2$ and water=1:1.2:2.1, 150 to 170° C. and (90 to 100)×10$^5$ N/m$^2$ (=90 to 100 bar).

The reaction conditions in the second stage are: 280 to 290° C. and (90 to 100)×10$^5$ N/m$^2$ (=90 to 100 bar).

WO 99/52867 (Pantochim S. A.) discloses a process for the continuous preparation of NMP by reaction of GBL with monomethylamine in the liquid phase in three successive reaction stages, with the first stage being operated at from 150 to 220° C., the second stage being operated at from 220 to 270° C. and the third stage being operated at from 250 to 310° C. The pressure in all three stages is in the range from 30 to 90 ATE (from 30.4 to 91.2 bar), preferably from 40 to 60 ATE (from 40.5 to 60.8 bar). The molar ratio of GBL to monomethylamine is from 1:1.05 to 1:1.4.

Chem. Abstract 82:139947 (JP-B4-49 020 585) describes the reaction of one part of GBL with two parts of monomethylamine and from 2 to 4 parts of water (=molar ratio of 1:5.5:9.6–19.1) at 250° C. (2 h) to give NMP in a yield of 99%. The temperature range for the reaction is generally from 200 to 300° C., in particular from 230 to 300° C.

Chem. Abstract 87:5802 (JP-A2-49 041 364) discloses the reaction of GBL with monomethylamine and water as a 1:1.4:4 mixture (=molar ratio of 1:3.9:19.1) at 250° C. and from 45 to 50 kg/cm$^2$ (=44 to 49 bar).

U.S. Pat. No. 2,964,535 (Monsanto) relates to a process for purifying NMP by treatment with an alkali metal hydroxide in aqueous solution and subsequent distillation.

It has been recognized according to the present invention that the prior art suffers from, inter alia, the following disadvantages:

a) low space-time yields of NMP, b) the use of relatively large amounts of water in the synthesis, which leads, inter alia, to high energy costs in the work-up of the reaction product mixture by distillation, c) the large molar excess of monomethylamine based on GBL, which results in a high engineering outlay in the work-up of the reaction product mixture and recovery of the unreacted monomethylamine and thus high capital and energy costs, and d) the high engineering outlay associated with high capital and operating costs when the reaction is carried out in a plurality of reaction stages, e.g. as described in WO 99/52867.

It is an object of the present invention to overcome the disadvantages of the prior art and discover an improved, selective process for preparing NMP in high yields and space-time yields and high quality (e.g. purity of >99.5% by weight, APHA color number of ≦50, residual GBL content of <0.05% by weight).

We have found that this object is achieved by a process for the continuous preparation of N-methyl-2-pyrrolidone (NMP) by reacting gamma-butyrolactone (GBL) with monomethylamine (MMA) in the liquid phase, wherein GBL and MMA are used in a molar ratio of from 1:1.08 to 1:2 and the reaction is carried out at from 320 to 380° C. and an absolute pressure of from 70 to 120 bar. The reaction according to the present invention is preferably carried out at from 330 to 380° C., in particular from 340 to 380° C., very particularly preferably from 350 to 370° C., e.g. 360° C.

The reaction according to the present invention is preferably carried out at an absolute pressure of from 70 to 110 bar, in particular an absolute pressure of from 80 to 110 bar, very particularly preferably an absolute pressure of from 80 to 105 bar, e.g. 90 bar.

The molar ratio of the starting materials GBL:monomethylamine in the process of the present invention is generally 1:(1.08–2.0), preferably 1:(1.08–1.5), in particular 1:(1.08–1.3), very particularly preferably 1:(1.08–1.2), most preferably 1:(1.08–1.15), e.g. 1:1.12.

The feed mixture generally contains less than 40% by weight, particularly preferably less than 10% by weight, very particularly preferably less than 5% by weight, in particular less than 1% by weight, of water. In a particularly preferred embodiment, the feed mixture does not contain any water.

The process of the present invention can, for example, be carried out as follows:

The reactor employed is preferably an upright, slender high-pressure tube which is equipped, after a heat exchanger with bypass, with a depressurization valve controlled via a pressure regulator. The feed streams are preferably preheated by the output from the reactor, so that the reaction temperatures specified according to the present invention can be set in the reactor by means of the heat evolved in the reaction. The reactor is preferably provided with a plurality of sieve trays to prevent back mixing and to improve the establishment of plug flow (effectively a cascade of stirred vessels). The number of sieve trays can be, for example, from 10 to 40, preferably from 20 to 30.

Liquid monomethylamine, if desired in admixture with recovered monomethylamine from the work-up (see below), is fed by means of a pump, e.g. a diaphragm pump, via a heat exchanger W2 and via a steam-operated heater W3 into the bottom end of the tube reactor (preferred upflow mode of operation).

GBL is likewise fed by means of a pump, e.g. a diaphragm pump, via a steam-operated heater W1 into the bottom end of the tube reactor, with mixing of the starting materials taking place and the starting materials GBL and monomethylamine being present in the abovementioned inventive molar ratio.

In a particularly preferred embodiment, the liquid monomethylamine and the GBL are fed separately into the tube reactor in the center of the bottom of the reactor via a two-fluid injector. While the GBL is introduced through the central nozzle at a high flow velocity (preferably 4–12 m/s), the liquid monomethylamine flows into the reactor through an annular gap around the outside of this nozzle. The starting materials are introduced as a driving jet into a circulation tube which is located in the inlet region of the reactor, encompasses about one third of the free cross section of the tube reactor and has a length of preferably from 1.5 to 2.0 m. The recirculation of liquid which occurs on the outside of the circulation tube and is maintained by means of the driving jet leads to intensive initial contact of the reactants in the above-described, inventive molar ratio.

Continuous exothermic reaction of the GBL with monomethylamine in the liquid phase to form NMP occurs in the reactor under the abovementioned temperature and pressure conditions.

The reaction is preferably carried out in the absence of a catalyst.

The mean residence times of the reaction mixture in the reactor or, if a plurality of reactors is used (cf. below), in all reactors are, on the basis of the density of GBL and monomethylamine (liquid) at room temperature (20° C.), are generally from 10 to 60 minutes, preferably from 15 to 30 minutes, depending on the throughput.

The space-time yields of NMP in the output from the reactor are generally $\geq 1$ kg of NMP/(h·$l_{reactor}$), preferably from 1 to 3 kg of NMP/(h·$l_{reactor}$), very particularly preferably from 1 to 2.5 kg of NMP/(h·$l_{reactor}$), e.g. 2 kg of NMP/(h·$l_{reactor}$).

($l_{reactor}$=reactor volume in liters; in the case of a plurality of reactors, total reactor volume in liters).

The reaction product obtained is continuously depressurized from the reactor as feed to a distillation column K1, with all or part of the output from the reactor firstly being passed through the heat exchanger W2 (see above) to heat the methylamine and being cooled in the process.

Overhead distillate from the distillation column K2 (main constituent:NMP, see below) can be mixed beforehand into the feed to the column K1.

In the distillation column K1, monomethylamine which is still present and water are distilled off, e.g. at from 40 to 240° C. and from 1 to 2 bar. Energy can be supplied by means of a circulation vaporizer. The distillate is generally a 15–30% strength by weight, in particular 15–25% strength by weight, e.g. about 20% strength by weight, aqueous monomethylamine solution. Anhydrous monomethylamine can be recovered from the solution by known methods.

The distillation of the monomethylamine still present and the water in this distillation step is preferably carried out in the presence of from 0.05 to 1% by weight, in particular from 0.05 to 0.2% by weight, very particularly preferably from 0.08 to 0.15% by weight, (in each case based on the amount of NMP in the feed to this distillation column) of hydroxides of the metals Na, K, Li, Ba or Ca.

The distillation of the MMA/water mixture in this distillation step is particularly preferably carried out in the presence of NaOH, which is metered as aqueous sodium hydroxide solution into the feed to the column K1 by means of a pump. For example, aqueous 25% strength sodium hydroxide solution is used in such an amount that the concentration of NaOH is from 0.05 to 0.2% by weight, in particular from 0.08 to 0.15% by weight (in each case based on the amount of NMP in the feed to this distillation step).

It has been recognized according to the present invention that this particular way of carrying out the process results in acidic components present in the reaction product (which could cause corrosion problems in the apparatuses) and any residual traces of unreacted GBL being bound (reaction of the GBL to form the corresponding metal salt of gamma-hydroxybutyric acid), so that a particularly pure NMP is finally obtained.

The bottoms are subsequently taken from the column K1, cooled if appropriate and conveyed by means of a pump to the column K2 for final distillation of the NMP. Pure NMP is isolated as a liquid stream at a side offtake of the column K2. The temperatures at the bottom are generally from 100 to 140° C. at from 0.01 to 0.02 bar. (Boiling point of NMP: 204° C./1 bar). Here too, heat can be supplied by means of a circulation vaporizer. The overhead distillate which comprises NMP together with MMA and water can be recirculated to the column K1 (see above) and/or to the reactor inlet.

The process of the present invention gives NMP in yields of >97%, in particular >97.5%, very particularly preferably >98%, after distillation.

The conversion of GBL is generally >99%, in particular >99.5%, very particularly preferably >99.9%.

The selectivity (based on GBL) is generally >97%, in particular >98%, very particularly preferably >99%.

The NMP obtained according to the present invention has a high quality after distillation:

The purity is generally >99% by weight, in particular $\geq 99.5\%$ by weight, very particularly preferably $\geq 99.8\%$ by weight.

The GBL content is generally <0.05% by weight, in particular <0.02% by weight, and the monomethylamine content is <50 ppm, in particular <20 ppm (ppm values are by weight).

The APHA color number in accordance with DIN ISO 6271 of the NMP obtained according to the present invention is generally $\leq 50$, in particular $\leq 20$.

The process of the present invention can also be carried out in an apparatus (tube reactor) as described in DE-A-17 95 007, which is hereby expressly incorporated by reference.

The process of the present invention is preferably carried out in a single stage, i.e. in a reactor which may, for engineering reasons, be divided into two or more apparatuses (reactors), with the pressure and temperature conditions specified according to the present invention then prevailing in each of these reactors.

In an alternative embodiment of the process of the present invention, a plurality of tube reactors (e.g. two or three reactors, each as described above) operated in the upflow mode can be connected in series, with the pressure and temperature conditions specified according to the present invention prevailing in at least one of these reactors, preferably in the last of these reactors.

An example of such a series arrangement of a plurality of reactors is given in WO 99/52867 (cf. the process flow diagram, reactors No. 5, 9 and 13, and the description in that document), which is hereby expressly incorporated by reference.

EXAMPLES

The synthesis of NMP was carried out continuously under the conditions indicated below in a tube reactor (RA4, length×internal diameter=2000 mm×30 mm, annular gap 9 mm, volume=1.1 l, electrically heated). The reactor was operated in a single pass in the upflow mode. The starting materials monomethylamine (MMA) and GBL were preheated and conveyed by means of pumps to the reactor inlet where the two streams were mixed. The total water content of the starting materials was less than 1% by weight.

A high-pressure separator was located at the reactor outlet, and the gas phase (nitrogen and inerts) was depressurized from this separator as offgas. The liquid phase which separated out was depressurized into a vessel at atmospheric pressure and excess MMA and water of reaction were subsequently distilled off as a mixture.

| | |
|---|---|
| Temperature: | 360° C. |
| Pressure: | 90 bar (pressure maintained by means of $N_2$) |
| Space velocity: | 1.4 kg of GBL/($l_{reactor}$ · h) |
| Molar ratio of GBL:MMA | 1:1.1 |
| Offgas | 20 standard l/h |

[Standard l = standard liters = volume converted to that at STP; space velocity through the reactor in kg of GBL per liter of reactor volume and hour].

The following table reports the composition of the reaction product mixtures (after evaporation of monomethylamine).

TABLE

GC analysis of the crude outputs from the NMP synthesis

| Experiment No. | NMP [GC-% by area] | GBL [GC-% by area] | DMP *) [GC-% by area] | Others [GC-% by area] |
|---|---|---|---|---|
| 1 | 99.5 | 0.02 | 0.15 | 0.33 |
| 2 | 99.6 | 0.01 | 0.19 | 0.2 |

GC conditions: 30 m DB-1, temperature program: 80° C. inlet temperature, 4° C./min. heating rate, 250° C. final temperature. The residual $H_2O$ content is disregarded.
*) DMP = 1,3-dimethyl-2-pyrrolidone and 1,4-dimethyl-2-pyrrolidone (formed from alpha- and beta-methyl-GBL, which were present as impurities in the GBL used).

The NMP yield in the crude output based on the GBL used was >99%. After purification by distillation, the NMP was obtained in a purity of >99.8% by weight.

The space-time yield of NMP in the crude output from the reactor was 1.5 kg of NMP/(h·$l_{reactor}$).

We claim:

1. A process for the continuous preparation of N-methyl-2-pyrrolidone (NMP) by reacting gamma-butyrolactone (GBL) with monomethylamine (MMA) in the liquid phase, wherein GBL and MMA are used in a molar ratio of from 1:1.08 to 1:1.3 and the reaction is carried out in a single stage at from 340 to 380° C. and an absolute pressure of from 70 to 120 bar.

2. A process as claimed in claim 1, wherein the reaction is carried out at from 350 to 380° C.

3. A process as claimed in claim 1, wherein the reaction is carried out at an absolute pressure of from 80 to 110 bar.

4. A process as claimed in claim 1, wherein GBL and MMA are used in a molar ratio of from 1:1.08 to 1:1.2.

5. A process as claimed in claim 1, wherein the reaction is carried out in an upright tube reactor.

6. A process as claimed in claim 5, wherein the reaction is carried out in the upflow mode.

7. A process as claimed in claim 5, wherein the monomethylamine and the GEL are fed separately into the tube reactor at the bottom of the reactor via a two-fluid injector.

8. A process as claimed in claim 1, wherein the reaction is carried out in the absence of a catalyst.

9. A process as claimed in claim 1, wherein the feed mixture contains less than 10% by weight of water.

10. A process as claimed in claim 1, wherein firstly water and monomethylamine and finally the N-methyl-2-pyrrolidone are distilled off from the reaction product after the reaction.

11. A process as claimed in claim 1, wherein the water and monomethylamine are distilled off from the reaction product in the presence of hydroxides of the metals Na, K, Li, Ba or Ca after the reaction.

12. A process as claimed in claim 1, wherein the N-methyl-2-pyrrolidone is isolated as a liquid stream from a side offtake of a distillation column.

13. A process as claimed in claim 1, for preparing N-methyl-2-pyrrolidone with a selectivity of >98%.

14. A process as claimed in claim 1, for preparing N-methyl-2-pyrrolidone having a purity of ≧99.5%.

15. A process as claimed in claim 1, for preparing N-methyl-2-pyrrolidone having an APHA color number of ≦20.

16. A process as claimed in claim 1, for preparing N-methyl-2-pyrrolidone in a space-time yield of ≧1 kg NMP/(h·$l_{reactor}$).

17. A process as claimed in claim 11, wherein the water and monomethylamine are distilled off from the reaction product in the presence of NaOH.

* * * * *

UNITED STATES PATENT AND TRADEMARK OFFICE
CERTIFICATE OF CORRECTION

PATENT NO. : 7,227,029 B2  Page 1 of 1
APPLICATION NO. : 10/495358
DATED : June 5, 2007
INVENTOR(S) : Rudloff et al.

It is certified that error appears in the above-identified patent and that said Letters Patent is hereby corrected as shown below:

In Claim 7, col. 6, indicated line 26: "GEL" should read --GBL--

In Claim 11, col. 6, indicated line 39: "Li. Ba" should read --Li, Ba--

Signed and Sealed this

Twenty-fifth Day of March, 2008

JON W. DUDAS
*Director of the United States Patent and Trademark Office*